United States Patent [19]

Kato

[11] Patent Number: 4,891,215

[45] Date of Patent: Jan. 2, 1990

[54] DEODORIZING MATERIAL

[75] Inventor: Taro Kato, Iwate, Japan

[73] Assignee: Kitakamiseishi Kabushiki Kaisha, Iwate, Japan

[21] Appl. No.: 171,384

[22] Filed: Mar. 21, 1988

Related U.S. Application Data

[63] Continuation of Ser. No. 932,001, Nov. 18, 1986, abandoned.

[51] Int. Cl.$^4$ .................. A01N 59/16; A61K 33/26
[52] U.S. Cl. .................. 424/76.5; 424/76.1; 424/76.9; 424/647
[58] Field of Search .................. 424/76.1, 76.5, 76.7, 424/76.9, 147

[56] References Cited

U.S. PATENT DOCUMENTS

| | | | |
|---|---|---|---|
| 4,306,516 | 12/1981 | Currey | 424/76 |
| 4,556,560 | 12/1985 | Buckingham | 424/131 |
| 4,637,820 | 6/1987 | Marini et al. | 8/129 |

OTHER PUBLICATIONS

The Merck Index, 10th Ed., (1983), p. 578, No. 3943.
Mikami et al., Chem. Abst. 103:58675k, (1985).
Sakai, Hiromu, Chem. Abst. 104:50364h, (1986).

Primary Examiner—Douglas W. Robinson
Attorney, Agent, or Firm—Rogers & Killeen

[57] ABSTRACT

A deodorizing material used for deodorization with respect to human and animal excreta by mixing at least one iron(II) or iron(III) compound selected from the group comprising ferrous sulfate, ferric sulfate, ferrous chloride, ferric chloride, ferrous nitrate, and ferric nitrate, in a cellulosic material and a cellulosic formed material.

12 Claims, No Drawings

DEODORIZING MATERIAL

This is a continuation of application Ser. No. 932,001 filed Nov. 18, 1986, now abandoned.

BACKGROUND OF THE INVENTION

1. Field of the Invention

The present invention relates to a deodorizing material exhibiting an excellent capacity to provide deodorization with respect to human and animal excreta.

2. Description of the Prior Art

With respect to deodorants for deodorizing human and animal excreta, various proposals have been made and brought into practice, but it cannot be said that an appropriate method has been employed in measuring deodorizing power.

In other words, conventional methods of measuring the deodorizing power of a deodorant include one in which a gas which causes malodor, such as ammonia, methylmercaptan, or hydrogen sulfide, is used for measuring the deodorizing power of a deodorant for such a gas, and one in which a deodorant is directly added to an aqueous solution of a substance which causes malodor, such as an ammonia, or methyl sulfide, so that the deodorizing power of the deodorant can be measured. Although the measurement results of the deodorizing power of deodorants obtained by these methods are sometimes to be seen, many of these results are not at all the same as those obtained by a measurement in which a deodorant is previously placed in a toilet bowl before a man or animal is allowed to defecate into the toilet bowl, and the strength of the resulting malodor is measured subjectively by the human nose.

Therefore, it is not apparent whether a deodorant showing excellent results using a gas or an aqueous solution of a substance which causes malodor is actually effective as a deodorant for human and animal excreta.

DETAILED DESCRIPTION OF THE INVENTION

As a result of vigorous investigations conducted by the inventor of the present invention for the purpose of developing a deodorizing material which is capable of effectively deodorizing the odor generated by excreta of humans and animals, the inventor has developed a deodorizing material which is capable of deodorizing to such an extent that no malodor is smelt by the human nose, when a man or animal is allowed to defecate into a toilet bowl in which the deodorizing material has previously been placed. The deodorizing material is characterized by comprising a cellulosic material such as wood fibers, cotton fibers, or the like as pulp or powder or is formed into sheets or fabric such as a paper diaper or gauze in which are contained at least one iron(II) or iron(III) compound selected from the group comprising ferrous sulfate, ferric sulfate, ferrous chloride, ferric chloride, and ferrous nitrate, and ferric nitrate.

DETAILED DESCRIPTION OF THE PREFERRED EMBODIMENTS

A description is given of an example of the present invention.

Example I (1) Preparation of deodorizing material 100 g of ferrous sulfate heptahydrate $FeSO_4.7H_2O$ was dissolved in water to prepare 1000 ml of an aqueous ferrous sulfate solution.

54.6 g of ferric sulfate $Fe_2(SO_4)_3$ was dissolved in water to prepare 1000 ml of an aqueous ferric sulfate solution.

A sheet of cellulosic pulp material containing 30% of pulp was torn into pieces, formed into a block of pulp having a diameter of about 5 mm, and then dried to a water content of 20%, thus preparing 1 kg of block of pulp.

Example I-1

90 ml of the above-prepared aqueous solution of ferrous sulfate heptahydrate $FeSO_4.7H_2O$ was added to 100 g of the above-prepared pulp block by spraying it with a spray and then put in an oven set at a temperature of 105° C. so as to be dried to a water content of 20%, preparing a block of cellulosic pulp deodorizing material.

Example I-2

90 ml of the above-prepared aqueous solution of ferric sultate $Fe_2(SO_4)_3$ was added to 100 g of the above-prepared pulp block by spraying it with spray and then put in an oven set at a temperature of 105° C. so as to be dried to a water content of 20%, thus preparing a pulp-block deodorizing material.

(2) Measurement of odor strength of excreta

Plastic buckets having covers were used as toilet bowls into which a predetermined amount of deodorizing materials used for testing deodorizing power were previously added. A panel of human subjects was asked to individually use these toilet bowls over period of 24 hours discharging both feces and urine thereinto. The covers of the toilet bowls were kept closed except during use.

The panel was asked to smell the odor generated from the toilet bowls when the covers were opened immediately before and after use so that the odor strength could be subjectively measured.

(3) Method of indicating odor strength of excreta

The following numbers were used to classify the strength of odor sensed by the panel.

TABLE 1

| Odor strength | Odor strength as detected by the human nose |
| --- | --- |
| 0 | No odor sensed |
| 1 | Odor barely sensed |
| 2 | Weak odor sensed |
| 3 | Strong odor sensed |

(4) Results of measurement of deodorizing power of deodorizing materials

The odor strength of excreta were measured in four sections in which, respectively, the deodorizing materials of the present invention (Examples I-1 and I-2), one deodorant on the market, and no deodorant had been previously placed. The results of these measurements are shown in Table 2. it can be seen from this table that the deodorizing materials of the present invention exhibit very excellent effects with respect to the deodorization of human excreta.

TABLE 2

| Section | Result |
| --- | --- |
| 50 g of example I-1 was used | Odor strength = 0 from the start to the end of the experiment |
| 50 g of example | Odor strength = 0-1 from the start |

TABLE 2-continued

| Section | Result |
| --- | --- |
| I-2 was used | to the end of the experiment |
| Comparison example (80 ml of a liquid deodorant on the market was used) | Odor strength = 0 from the start of the experiment for a period during which the amount of excreta gathered in the toilet bowl was small, but the odor strength had increased to 2–3 by the end of the experiment. |
| Comparison example (no deodorant was used) | Odor strength = 1 in the state wherein only urine had collected in the toilet bowl at the start of the experiment, but the odor strength had increased to 3 after defecation. |

At the end of the experiments, the excreta collected in the toilet bowl was a mixture of feces and urine in amounts of about 2 to 3 liters per toilet bowl.

Example II (1) Preparation of deodorizing materials
Example II-1

180 ml of a aqueous solution ferrous sulfate heptahydrate $FeSO_4.7H_2O$ prepared in Example I was added to a sheet of water absorbing material, e.g., an adult paper diaper, [specification ... absorbing paper (pulp 100%), width 300 mm, length 650 mm, 10 sheets, total weight 63 g] by spraying it with a spray and then put in an oven set at a temperature of 105° C. and dried to a water content of 15%, thus preparing an adult paper diaper as a deodorizing material.

Example II-2

A deodorizing material was prepared in the same way as Example II-1 except that an aqueous ferric sulfate solution was used in place of the aqueous ferrous sulfate solution used in the above Example II-1.

(2) Measurement of odor strength of excreta

The above-prepared adult paper diapers were put on a bedridden man (75 years old) at 10 a.m. and removed at 5 p.m. and the odor strength of excreta was estimated by the attendant smelling the odor generated by the paper diapers.

(3) Method of indicating odor strength of excreta

The same method as in Example I (4) Results of measurement of deodorizing power of adult paper diapers as deodorizing materials The odor strengths of excreta on three paper diapers comprising the adult paper diapers as deodorizing materials (Example II-1 and Example II-2) and an adult paper diaper which has not been treated were measured. The results are shown in Table 3. It can be seen from the table that the adult paper diapers as the deodorizing materials of the present invention exhibit very excellent effects with respect to the deodorizatin of human excreta.

TABLE 3

| Section | Result |
| --- | --- |
| Example II-1 | Odor strength = 1 (excreta of urine alone) |
| Example II-2 | Odor strength = 1 (excreta of urine alone) |
| Comparison example (untreated diaper) | Odor strength = 3 (excreta of urine alone) |

The excreta of the bedridden old man who was the subject of the test was only urine for the period of the above-mentioned time, as described above.

Example III (1) Preparation of deodorizing materials
Example III-1

180 ml of the aqueous ferrous sulfate heptahydrate $FeSO_4.7H_2O$ prepared in Example I was applied to a piece of gauze available on the market (width 300 mm, length 5000 mm, weight 53 g) by spraying it with a spray and then put in an oven set at a temperature of 105° C. and dried to a water content of 15%, thus preparing a gauze as a deodorizing material. This gauze was cut into a square having four equal sides of 30 mm so as to prepare a gauze deodorizing material.

Example III-2

A deodorizing material was prepared by the same method as Example III-I except that aqueous ferric sulfate solution was used in place of the aqueous ferrous sulfate heptahydrate solution $FeSO_4.7H_2O$ used in Example III-1.

(2) Measurement of odor strength of excreta The same method as in Example I.

(3) Method of indicating odor strength of excreta The same method as in Example I.

(4) Results of measurements of deodorizing power of the gauze deodorizing materials.

The odor strengths of excreta in three gauze deodorizing materials comprising the gauze deodorizing materials of the present invention (Example III-1 and Example III-2) and an untreated gauze were measured in a similar manner to Example I, with the results shown in Table 4 obtained. It can be seen from this table that the deodorizing materials of the present invention exhibit very excellent effects in respect of the deorization of human excreta.

TABLE 4

| Section | Result |
| --- | --- |
| Example III-1 | Odor strength = 0–1 from the start to the end of the experiment. |
| Example III-2 | Odor strength = 0–1 from the start to the end of the experiment. |
| Comparison example (untreated gauze) | Odor strength = 1 in the state wherein only urine had collected in the toilet bowl, at the start of the experiment, but the odor strength had increased to 3 after defecation. |

All the above examples relate to the cases in which odor generated from human excreta is deodorized by using an aqueous solution of ferrous sulfate or ferric sulfate, but the present invention is not limited to these cases. If an aqueous solution of ferrous chloride, ferric chloride, ferrous nitrate, or ferric nitrate is used, and if the deodorizing materials of the present invention are applied to deodorize the odor of excreta of animals such as pets, the same effects can be obtained.

EFFECT OF THE INVENTION

As described above, the present invention is preferred as a deodorizing material for deodorizing odor generated from excreta of humans or animals. In particular, the invention is effective used to suppress of the odor from excreta of bedridden old people which has recently become a noted social problem.

What is claimed is:

1. A method for manufacturing deodorizing materials comprising cellulosic substances containing iron salts, comprising the steps of:

(a) spraying an aqueous ferrous sulfate solution on a cellulosic substance; and
(b) drying the sprayed cellulosic substances at a temperature of approximately 105° C. for a period of time sufficient to form an oxidizing $Fe^{+++}$/cellulosic substance complex.

2. A method in accordance with claim 1 wherein said sprayed cellulosic substances are dried until such time as a moisture content of between 15 and 20% is achieved.

3. A method of manufacturing a deodorizing material comprising the steps of:
   (a) impregnating a material containing cellulose fibers with a solution of ferrous salts taken from the group consisting of sulfates, chlorides and nitrates; and
   (b) drying the impregnated cellulose fibers at a temperature of approximately 105° C. until the moisture content of the impregnated cellulose fibers is between 15 and 20% to evaporate the solution and form an oxidizing $Fe^{+++}$/cellulose fibers complex.

4. The method of claim 3 wherein said ferrous salts are in an aqueous solution.

5. The method of claim 3 wherein said ferrous salts are sulfates.

6. The method of claim 3 wherein the cellulosic fibers include at least one of wood fibers and cotton fibers.

7. The method of claim 3 wherein the cellulosic fibers are in the form of at least one of a sheet material and particulate material.

8. A deodorizing material comprising an $Fe^{+++}$/cellulose complex prepared by:
   (a) preparing a solution of iron salts selected from the group consisting of ferrous sulfates, ferrous chlorides, and ferrous nitrates;
   (b) impregnating a cellulosic or cellulosic formed material with said solution; and
   (c) drying said material for a period of time and at a temperature of approximately 105° C. to form an oxidizing $Fe^{+++}$/cellulose complex.

9. A deodorizing material according to claim 8 in which said cellulosic material includes at least one of wood pulp fibers, natural cotton fibers, or regenerated fibers.

10. A deodorizing material according to claim 8 in which said cellulosic formed material is in the form of at least one of a sheet, paper, powder, block, cotton, or cloth.

11. A deodorizing material in accordance with claim 8 in which said solution is an aqueous ferrous sulfate solution.

12. A deodorizing material according to claim 8 in which said material is dried to have a moisture content of 15 to 20%.

* * * * *